United States Patent [19]

Gattamorta

[11] Patent Number: 5,787,508
[45] Date of Patent: Aug. 4, 1998

[54] DECORATIVE MASK ASSEMBLY

[76] Inventor: Ruben D. Gattamorta, 9375 Fountainblue Blvd., #L-217, Miami, Fla. 33172

[21] Appl. No.: 808,983

[22] Filed: Feb. 19, 1997

[51] Int. Cl.[6] .................................................. A42B 1/00
[52] U.S. Cl. .................................. 2/206; 2/9; 2/DIG. 10
[58] Field of Search ........................ 2/9, 206, DIG. 3, 2/DIG. 10, 424, 173

[56] References Cited

U.S. PATENT DOCUMENTS

2,664,567  1/1954  Nichols .................................... 2/9

*Primary Examiner*—Diana Biefeld
*Attorney, Agent, or Firm*—Malloy & Malloy, PA

[57] ABSTRACT

A decorative mask assembly having a first and a second flexible material panel, and at least one perimeter securement segment defined generally about a perimeter of the first and second flexible material panels so as to define an interior chamber structured to receive and contain a quantity of a gas therein. The assembly further including a plurality of interior securement segments defined between the first and second flexible material panels and which at least partially defining a plurality of interior compartments in the interior chamber. The plurality of interior securement segments and the plurality of interior compartments defined thereby are structured and disposed relative to one another so as to define a predetermined, three-dimensional, ornamental, exterior surface configuration in the second flexible material panel, that corresponds a desired three dimensional depiction, and to provide shape defining stiffness to the first and second flexible material panels upon introduction and containment of the gas in the interior compartments, and to define an interior surface contour of the first flexible material panel that substantially conforms to a curvature of the user's face as the mask assembly is structured to be oriented and maintained in a generally vertical plane, in confronting relation to the user's face.

42 Claims, 4 Drawing Sheets

DECORATIVE MASK ASSEMBLY

BACKGROUND OF THE INVENTION

1. Field of the Invention

The present invention relates to a decorative mask assembly structured to be worn in confronting relation over a user's face in order to achieve an attractive and enhanced three dimensional, ornamental configuration. The present invention further relates to a decorative mask assembly which includes at least a goggle region structured and disposed to conform to the morphology and/or contours of the human face, and further, to provide a generally stiff, and yet contoured, esthetically pleasing three-dimensional appearance.

2. Description of the Related Art

The field of art relating to decorative and ornamental masks to be worn over a user's face is quite crowded, and a variety of different ornamental and decorative enhancements have been offered over the years. Indeed, it is often the visual effect or appearance of those ornamental enhancements which make the masks unique relative to one another. For example, cloth or fabric masks have been provided so as to provide some masking or covering of the human face and to achieve certain decorative designs. In more recent years, masks have been devised of latex and/or rubber which are slid onto a person's head to provide a specific ornamental and decorative appearance. Typically, this type of mask has been defined by the latex during manufacture about a molded form such as of a celebrity, a politician, an animal or beast, or other such similar decorative and ornamental configuration. While these traditional types of masks have become quite common, particularly for celebrating Halloween, they nonetheless possess certain drawbacks. As a result, a new mask assembly which provides a uniquely attractive three dimensional configuration would be desirable. Specifically, such a unique mask configuration should not only be easy and comfortable to wear, but also to store in a convenient manner, while also being capable of achieving a vast variety of different, uncommon and even whimsical, three dimensional designs and configurations. Ideally, any such unique mask configuration would not require heavy, time-consuming and/or cumbersome structures for forming masks, as are required with the known molded latex masks.

Also in the past, others have developed a variety of mask configurations which include one or more inflatable pockets. Generally, these masks are defined by a conventional fixed structure with inflatable pockets designed as novelty features, such as to define a pair of bulging eyes on a face, and thus, are in addition to the underlying fixed mask structure. In particular, these mask assemblies do not provide a plurality of inflatable pockets which function together and which are defined in such a manner that the decorative mask assembly itself is given its overall shape and form. Rather, known mask configurations are known to include a conventional, rigid, shape-defining structure with the inflatable pockets providing only an added novelty feature. As such, there remains a need in the art for a novel mask assembly having structural improvements whereby a three dimensional, ornamental shape is formed by inflatable pockets within the mask, and further, which is structured to conform to the contours of the human face so as to aid in providing sufficient stiffness to the mask, and to aid in providing an even and balanced appearance which resists the collapse of distal mask portions. Any such improved mask assembly should be relatively easy and cost effective to manufacture, so as to result in a relatively inexpensive item for purchase, and further, should be convenient to use and to store for future use.

In addition to those mask assemblies which are directed towards providing some ornamental configuration, it is noted that other inflatable structures have been developed in the past for a variety of different purposes. One example of such an inflatable structure is a typical balloon. Such structures, however, are typically not capable of being worn on the human face and in any event, are not structured to define a mask which includes an enhanced three-dimensional configuration which conforms to the contours of the human face. For example, even if one were able to define an eye opening in a conventional balloon structure, so as to be usable as a mask for the face, the resulting structure would still not be capable of defining a particular three dimensional shape and configuration. Specifically, a conventional balloon merely provides a surface onto which indicia is disposed and does not function to enhance the ornamental depiction in the manner of a mask that is worn in front of a user's face and that conforms to the general curvature of the face. Another example of an inflatable structure is a small mask formed to cover the eyes of a wearer which may be filled with a gas or a gel. Such eye masks, however, generally provide a single inflatable compartment, and further, their appearance is defined by the shape given to that single compartment. In this regard, such known eye masks cannot offer an attractive and enhanced three dimensional, ornamental configuration which conform to the morphology of the human face, and which provide a generally stiff, and yet contoured appearance. In this regard, the shape of known eye mask devices is thought to be dictated by their function, namely, to cover the eyes so as to provide darkness and/or to rest directly over the eyes so as to provide cool comfort to aid in relaxing the user. As such, known eye mask devices are not structured to provide a mask, with eye portions designed to permit easy viewing, let alone, a mask that defines an ornamental, three dimensional configuration.

Finally, it is noted that a variety of inflatable objects have been developed for use on a person's head, but which do not relate to decorative masks. Generally, these devices include helmets or other impact-absorbing devices specifically structured to minimize the effects of a severe impact to a wearer's head. Some devices of this type incorporate a number of air pockets to absorb impact and/or to distribute the impact over the wearer's head. Such helmet type of deices in no way provide a decorative mask assembly which offer a decorative, three dimensional configuration. Furthermore, such helmets are naturally designed to fully cover the wearer's head, and therefore, could not be disposed in a generally vertical orientation adjacent to and in confronting relation with a wearer's face, let alone to conform to the curvature of a wearer's face. In this regard, the structure of such helmet devices is thought to be dictated by their function, namely, to deaden or lessen the force of a blow to a person's head. As such, such helmet devices are not capable of defining a decorative mask assembly having a three dimensional ornamental shape, which offers sufficient stiffness to even distal portions of the mask so as to prevent collapse, and which enables the mask to generally conform to the wearer's face. In fact, such devices of the unrelated art associated with helmets have taught away from improvements and structure such as that presented in the present invention. For example, helmet devices which include one or more air pockets to absorb an impact to the head generally require an exterior material covering that defines the overall shape of the helmet, as clearly, the air pocket compartments themselves and any walls between them are sandwiched within the helmet covering and further, merely provide a barrier to separate one compartment from the other rather than to define an ornamental, contoured mask assembly.

SUMMARY OF THE INVENTION

The present invention is directed towards a decorative mask assembly to be disposed in confronting relation over a user's face and is structured to be inflatable for use and to be deflated for storage purposes. Upon being inflated, the decorative mask assembly of the present invention is structured to provide a three dimensional ornamental configuration in front of the user's face which both conforms to the curvature of the human face and possesses sufficient stiffness to prevent collapse of even distal portions of the decorative mask assembly.

More in particular, the decorative mask assembly includes a first and a second flexible material panel. The flexible material panels are generally secured to one another about their corresponding perimeters or in the preferred embodiment, by at least one perimeter securement segment defined generally about a perimeter of the first and second flexible material panels. The first and second material panels, in combination with the perimeter securement segment, define an interior chamber between the first and second material panels. Within the interior chamber, which is preferably fluid impervious, a quantity of a gas, such as air, is received and contained.

Additionally, the mask assembly includes a plurality of interior securement segments. The interior securement segments are defined generally between the first and second flexible material panels, and are structured to define a plurality of interior compartments. The interior securement segments and the plurality of interior compartments defined thereby, are structured and disposed relative to one another so as to define a predetermined, three dimensional, ornamental, exterior surface configuration in the second flexible material panel. Moreover, that predetermined, three dimensional, ornamental, exterior surface configuration corresponds a desired three dimensional character or other fanciful image, thereby providing an enhanced and attractive appearance to the decorative mask assembly. Also, the plurality of interior securement segments, and the plurality of interior compartments defined thereby, are structured and disposed to provide a shape defining stiffness to the first and second flexible material panels, upon introduction and containment of a gas within the interior chamber. As a result, the mask assembly will independently maintain its attractive and ornamental three dimensional shape, in the inflated state. Further, the plurality of interior securement segments, and the interior compartments defined thereby, are additionally structured and disposed relative to one another so as to define an interior surface contour of the first flexible material panel. The interior surface contour is structured to substantially conform to a curvature of the user's face, thereby providing a more attractive and more enhanced ornamental three dimensional appearance to the mask when worn on the wearer's head.

In the preferred embodiment, the present invention additionally comprises fastening means to orient and maintain at least the first flexible material panel of the mask in both a generally vertical plane and in confronting relation to the user's face. The fastening means are operably coupled to or connected to the decorative mask assembly, preferably to opposite sides of the first flexible material panel, and are utilized to position the mask assembly on the wearer's head, ideally by extending about and behind the user's head.

It is an object of the present invention to provide a mask assembly which is to be disposed in confronting relation to a user's face and which can maintain, substantially independently, an attractive and predetermined three dimensional configuration.

A further object of the present invention is to provide a mask assembly which is structured to generally conform to the curvature of the human face.

Still another object of the present invention is to provide a mask assembly which is configured to be substantially reversible, and to maintain its ornamental, three dimensional shape in both the initial and reversed attitudes.

Yet another object of the present invention is to provide a mask assembly which provides a goggle region for being positioned generally over and corresponding to the wearer's eye region, and which further includes a nose section that protrudes generally outwardly so as to receive a wearer's nose comfortably.

An additional object of the present invention is to provide a mask assembly which is structured and configured to direct the forces exerted on the first and second flexible material panels when inflated, in more than one desired direction so as to achieve a unique three dimensional configuration that conforms to the curvature of a user's face, and prevent collapse of even distal portions of the decorative mask assembly.

Yet another object of the present invention is to provide a decorative mask assembly which is structured to enable different regions thereof to be extended into specific, different, desired planes relative to one another in order to provide a unique, esthetically pleasing, three dimensional configuration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Shown throughout the Figures, the present invention is directed towards a decorative and inflatable mask assembly, generally indicated as 10. The inflatable decorative mask assembly 10 is structured to be inflated with a gas, such as air, in order to define an attractive and decorative, three dimensional configuration to be worn by a user in a wide variety of desired activities. The decorative mask assembly 10 is substantially lightweight and is easy and cost-effective to manufacture. The mask assembly 10 is further inexpensive to purchase, easy to utilize, and yet, is highly adaptable to form a myriad of configurations and desired, decorative characters or other images. The selected configuration, which is defined as a result of the structure and configuration of the mask assembly 10 about to be described, may be varied depending upon the needs, desires or whims of a particular user, and similarly, any graphical indicia disposed on or adhered to the decorative mask assembly 10, can also be varied as well.

The decorative mask assembly 10 of the present invention is initially seen to include a first flexible material panel 22 and a second flexible material panel 20. The first and second flexible material panels are generally sized to correspond a desired dimension of the overall mask assembly 10. Moreover, the flexible material panels 20 and 22 may be formed of a light weight material, such as a conventional, balloon making material. Preferably, an inelastic material will be utilized in forming flexible material panels 20 and 22, as it will allow for a more precise definition of the desired three dimensional configuration to result upon inflation of the mask assembly 10 according to the present invention.

The first and second flexible material panels 20 and 22 of the present invention are preferably secured to one another generally along their perimeters such as by a fluid impervious adhesive, stapling means, sewing means, etc., so as to form an interior chamber 25 therebetween. Alternatively, included generally about a perimeter of the first and second flexible material panels 22 and 20 in the preferred embodiment is at least one perimeter securement segment 30. The perimeter securement segment, which may be one complete continuous segment 30, as in the preferred embodiment, may also include a series of segments spaced by an alternative fluid impervious section, is structured to define an interior chamber between the first and second flexible material panels 22 and 20. The perimeter securement segment 30 is structured to be substantially fluid impervious and in the preferred embodiment, is defined directly between the first and second flexible material panels 20 and 22, ideally by a heat seal, that adheres the flexible material panels 20 and 22 directly to one another to form the perimeter securement segment 30. As such, the interior chamber is defined and is structured to receive and contain a quantity of gas therein when the mask assembly 10 is to be utilized and is to be given its defined shape as a result of inflation.

Figure 1:
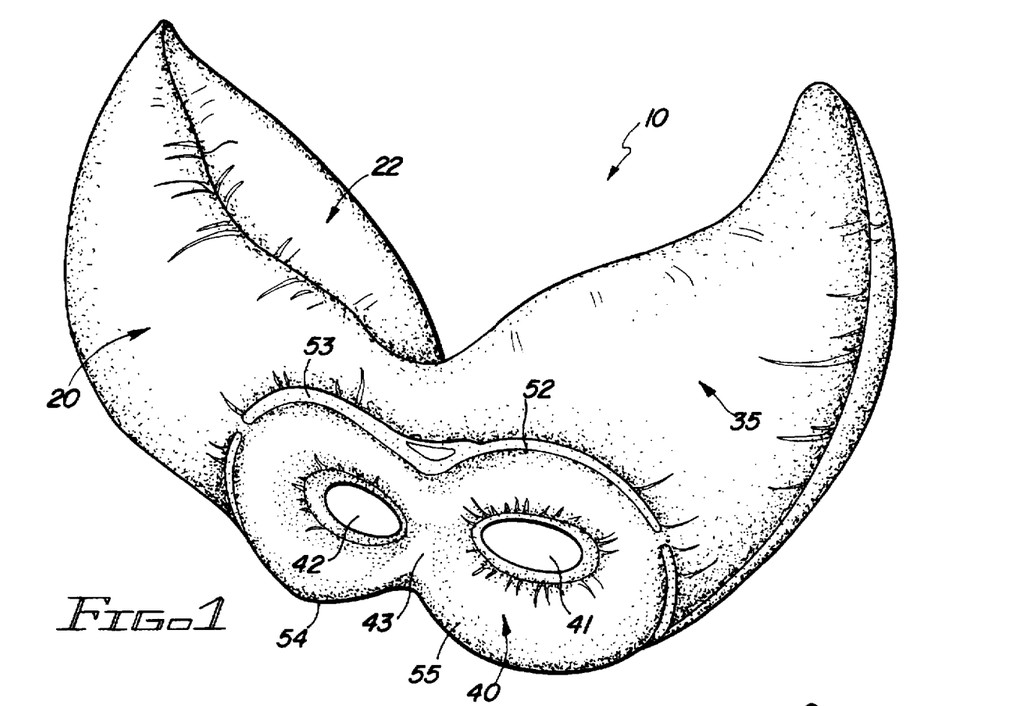
FIG. 1 is a perspective view of a decorative, inflatable mask assembly according to the present invention.
Figure 2:
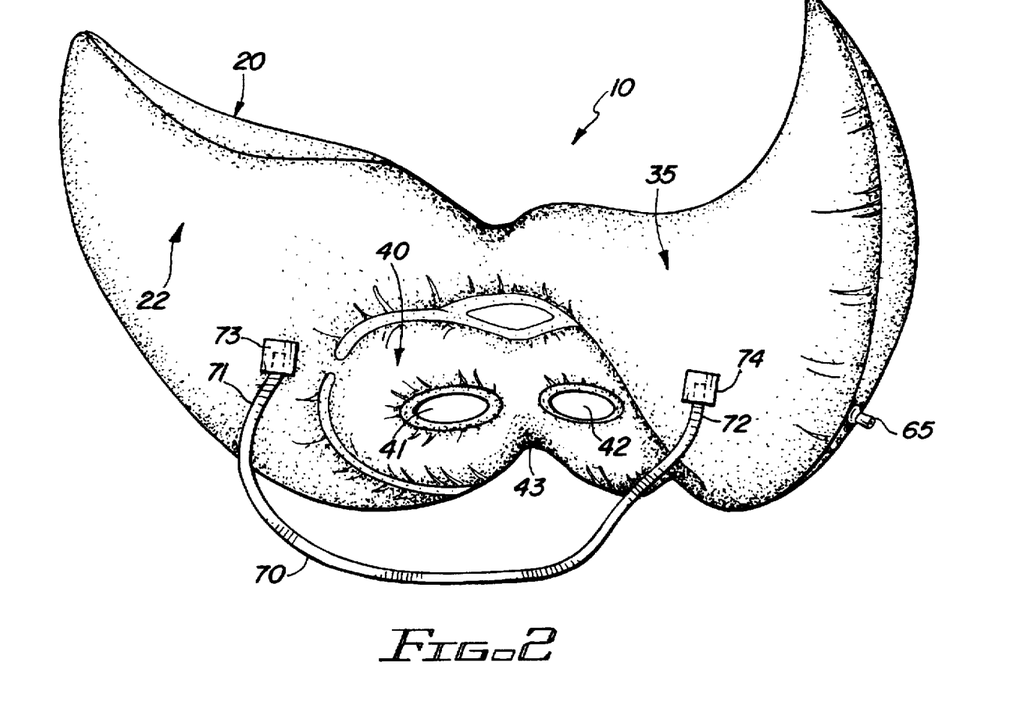
FIG. 2 is a rear perspective view of the decorative, inflatable mask assembly illustrated in FIG. 1.

The decorative mask assembly 10 of the present invention further includes a plurality of interior securement segments 52, 53, 54, 55 and 56. The total number of the interior securement segments depends on the desired, three dimensional character or other image which is to be achieved by the mask assembly. Moreover, it will be appreciated that with certain design configurations, such as depicted in FIG. 1, one or more of the interior securement segments 54, 55, may have a dual function in that they also function as part of the perimeter securement segment 30. As with the perimeter securement segment 30, it is preferred that the interior securement segments also be defined by a heat seal formed directly between the first and second flexible material 22 and 20. The seal, however, should be substantially strong such that upon inflation of the mask assembly 10, the seals are not broken under the pressure of the gas introduced therein.

It is seen that the plurality of interior securement segments 52, 53, 54, 55 and 56 defined between the first and second flexible material panels 20 and 22 at least partially define a plurality of interior compartments 25 in the interior chamber. These interior compartments 25 are preferably disposed in fluid flow communication with one another and may be completely and/or partially separated from one another by one or more of said interior securement segments.

The plurality of the interior securement segments 52, 53, 54, 55, 56, and the plurality of interior compartments 25 defined thereby, are structured and disposed relative to one another so as to define a predetermined, three dimensional, ornamental, exterior surface configuration in and from the second flexible material panel 20. For example, the exterior surface configuration may correspond to a desired three dimensional depiction such as a devil head, an animal head, a mardi gras type head dress, etc. In particular, the specific orientation and spacing of the interior securement segments define to what extent the first and second flexible material panels 20 and 22 can separate from one another to form the defined interior compartments 25. Also, such limitations and precise orientation of the various interior compartments and interior securement segments direct the forces which act upon the flexible material panels in directions that work together to define the overall shape.

Moreover, it is seen that the particular size and orientation of the interior securement segments 52, 53, 54, 55, 56, and the plurality of interior compartments 25 relative to one another also provides a shape defining stiffness to the first and second flexible material panels 20 and 22, once the gas, such as air, is introduced and contained within the interior compartments 25. In this regard, the interior securement segments 52, 53, 54, 55, 56 define an interior surface contour of the first flexible material panel 22 that substantially conforms to a curvature of the user's face, in a manner which will be described shortly.

In the preferred embodiment, the mask assembly 10 of the present invention is divided primarily into a goggle region, generally 40, and a perimeter design region, generally 35. Specifically, the goggle region 40, as defined by the plurality of interior securement segments 52, 53, 54, 55, 56 and the plurality of interior compartments 25, is structured to be disposed generally over a user's eyes and the front region of the user's face. In particular, in an embodiment wherein no particular eye openings are provided, the goggle region defines the area in confronting relation to the face of the wearer. Preferably, however, the goggle region 40 comprises at least one, and more preferably, a pair of spaced apart eye regions 41 and 42. The eye regions 41 and 42 are structured to be disposed over and to generally correspond one or both of the user's eyes in order to permit viewing therethrough when the mask assembly 10 is being worn by the user. Moreover, the goggle region 40 is also preferably symmetrical about a central vertical axis A thereof, illustrated in FIG. 4, so as to substantially conform and maintain the interior surface contour of the first flexible material panel 22 to the curvature of the user's face. In particular, the mask assembly of the present invention is specifically structured and configured, as a result of the positioning of the interior securement segments and interior compartments, to correspond the morphology of a typical human face. As such, the mask assembly 10 of the present invention tends to be curved and to partially around the wearer's face into a more conforming and more attractive configuration. This contouring of the mask assembly 10 to the curvature of the wearer's face generally defines a forward, concave, and fully reversible configuration. For example, because of the general symmetry, the general stiffness and particular definition which is achieved as a result of the interior securement segments 52–56, and interior compartments 25, the mask assembly 10 can be reversed providing for more than one, three dimensional graphical representation utilizing the same mask assembly 10. Continuing with this example, one of the flexible material panels 20 may include particular graphical indicia thereon while the other flexible material panel 22 includes different graphical indicia thereon, both of which nonetheless correspond the three dimensional structural configuration achieved by the mask assembly 10. In this regard it is preferred that a non-toxic substance or material be utilized to imprint the graphical indicia, or in the alternative, the interior side of one of the flexible material panels could be made to be transparent, with only the exterior material panel bearing differing indicia on opposite sides thereof. In this alternative embodiment, when the mask assembly 10 is reversed, the inside indicia is seen through the transparent material forming the one side flexible material panel.

According to the present invention, it is preferred that the goggle region 40 be dimensionally symmetrical about the central vertical axis A. In particular, the position of the interior securement segments 52–56 and therefore, the size and position of the interior compartments 25 defined thereby should be substantially equal to the left and right side of the central vertical axis A at the goggle region 40.

Additionally, the goggle region 40 includes a nose section 43. The nose section 43 is structured to substantially confront and correspond a user's nose. Moreover, as a result of the positioning of interior securement segments 52–56 which define the nose section, the nose section 43 tends to be maintained in a generally forward, protruding orientation, thereby more effectively accommodating the user's nose. Indeed, in a reversed configuration this nose region is merely pushed in and the outward protrusion is maintained merely in an opposite direction. Still, as a result of the configuration of the interior securement segments 52–56, protrusion out of the completely vertical plane is achieved and maintained.

Figure 4:
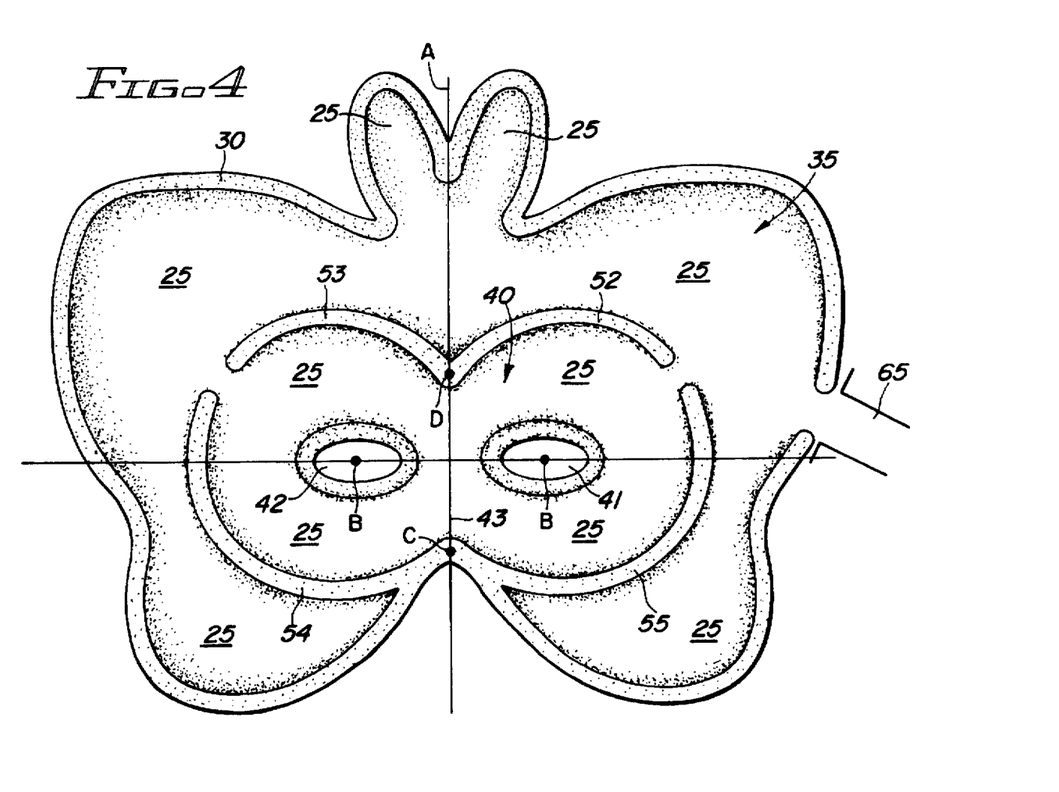
FIG. 4 is a cross-sectional view of an alternative embodiment of the decorative, inflatable mask assembly of the present invention.

As indicated, the interior securement segments 52–56 and the interior compartments 25 defined thereby are positioned in such a manner so as to define the three dimensional configuration and provide a surface contour which generally conforms to the morphology of the human face. In the preferred embodiment, such a configuration is achieved by a particular positioning of some of the interior securement segments so as to define the goggle region 40. In particular, and as best illustrated in the FIG. 4, at least two of the interior securement segments 54 and 55 are structured and disposed to converge towards a first axis point, C defined on the central vertical axis A of the goggle region 40. The two interior securement segments 54 and 55 will converge towards the first axis point C, and may or may not actually engage one another, depending upon the desired ornamental configuration. Furthermore, the first axis point, C, is preferably disposed at a point below a center point, B, of the eye regions 41 and 42, as shown in FIG. 4. Specifically, in the preferred embodiment, the center points, B, of the eye regions 41 and 42 are symmetrically disposed relative to one another about the central vertical axis A. Moreover, the eye regions are preferably open and are defined by an eye perimeter securement segment 45, such as a heat seal about the eye regions 41 and 42. In the preferred embodiment, the central point, B, of the spaced apart eye regions 41 and 42 provides a reference point for the positioning of the first axis point C. When defining that point, a circle having a radius that extends generally from the central point, B, of for example, the eye region 42, to the eye perimeter securement segment 45 of the other eye region 41 is drawn. A similar circle is likewise drawn for the other eye region 41 with the point of convergence of those circles on the central vertical axis, A, defining the first axis point C, and a second axis point D, as will be described subsequently. Such positioning of the securement segments is of course preferably achieved on a preformed, heat sealing die.

In the first embodiment, at least the first axis point C is required as the convergence of the securement segments 54 and 55 towards that first axis point C functions to substantially achieve the corresponding morphological curvature as well as to define the nose segment 43. Moreover, in the preferred embodiment, the first axis point C is disposed within a range of approximately two inches or less from the eye perimeter securement segments 45 of the eye regions 41 and 42, as this will provide for an appropriate direction of forces and appropriate orientation of the goggle region 40.

Figure 5:
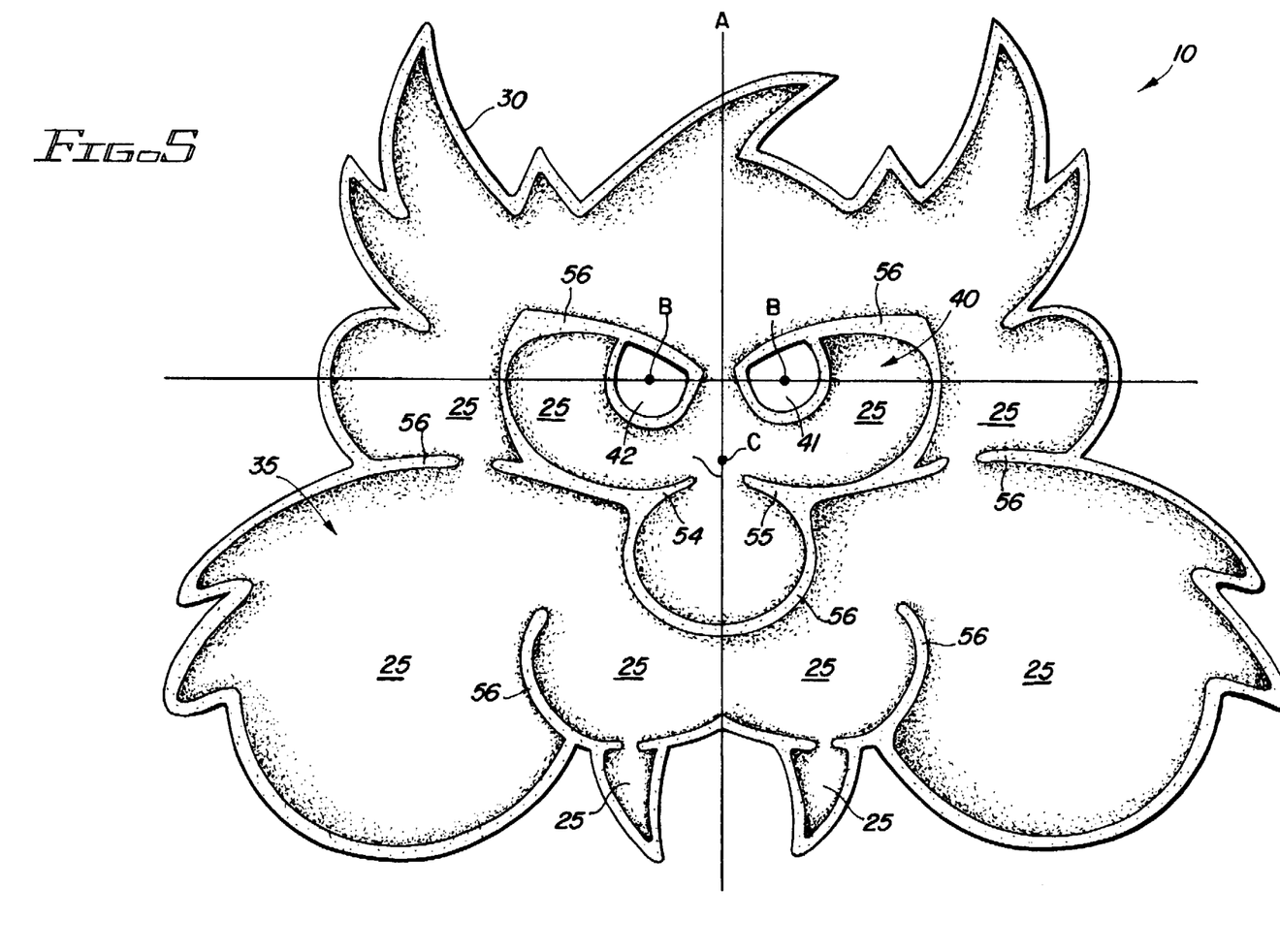
FIG. 5 is a cross-sectional view of another alternative embodiment of the decorative, inflatable mask assembly of the present invention.
Figure 6:
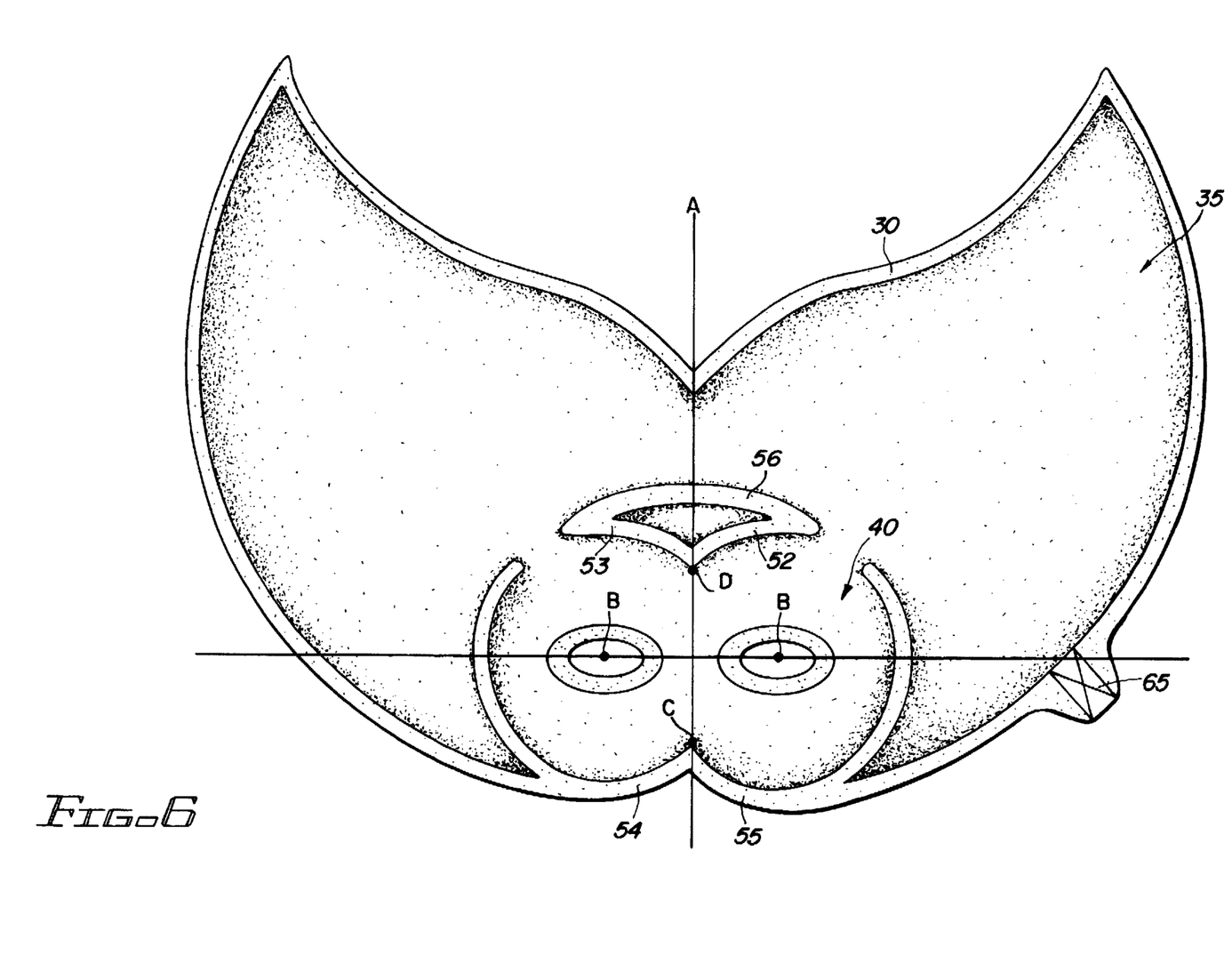
FIG. 6 is a cross-sectional view of a further alternative embodiment of the decorative, inflatable mask assembly of the present invention.

As indicated, a second axis point, D, may also provided, although it is not absolutely required. In the preferred embodiments, at least two interior securement segments 52 and 53 converge towards the second axis point, D, to further enhance and define the desired configuration. Incorporation of this second axis point D is illustrated in FIGS. 4 and 6. However, as shown in FIG. 5, for a more detailed graphical depiction wherein a majority of the structure extends beneath the eye regions 41 and 42, merely the interior securement segments 54 and 55 which converge towards the first axis point C are necessary. In this embodiment, yet another lower axis point on the central vertical axis A may also be defined and may include convergent interior securement segments correspondingly provided. As such, the curvature which conforms to the user's face is achieved, and the nose region is provided beneath the first axis point C to accommodate the user's nose in relation to the positioning of their eyes at the eye regions 41 and 42.

Figure 3:
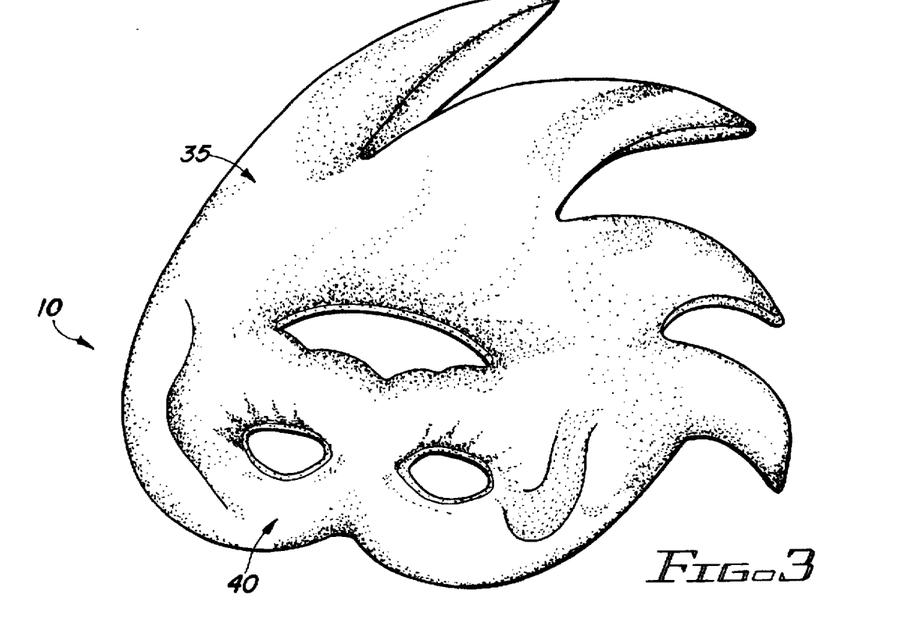
FIG. 3 is a front view of a decorative mask assembly of the present invention in an inflated state and illustrating a first embodiment.

As described previously, the present invention comprises in addition to goggle region 40, a perimeter design region 35. Preferably, the perimeter design region 35 is also symmetrical about the central vertical axis A, shown in FIGS. 4 and 5. The perimeter design region 35, however, may be dimensionally symmetrical as with the goggle region 40, or volumetrically symmetrical as shown in the embodiment of FIG. 3. In particular, even though the goggle region 40 may be volumetrically symmetrical, it is preferably dimensionally symmetrical indicating that the size of the interior compartments 25 and the positioning of the interior securement segments are equal on both sides of the central vertical axis, A. The same is true with the perimeter design region 35, however, as some ultimate design depictions may require some variations from one side to another, the perimeter design region 35 which provides the enhanced exterior and embellished design to the predetermined, three dimensional, ornamental, exterior surface configuration, may include volumetric symmetry wherein the volume of gas contained to one side of the central vertical axis is the same as the volume of gas contained on the opposite side of the central vertical axis.

From the previous description, it is seen that the positioning of the interior securement segments and interior compartments 25 is such that the forces which act upon the first and second flexible material panels 20 and 22, once the mask assembly 10 is inflated, may be precisely directed. These forces are directed so as to define the interior surface contour of the first flexible material panel 22 to correspond the morphology of the user's face, as well as to define the predetermined, three dimensional, ornamental, exterior surface configuration. Moreover, because of the direction of forces, the exterior surface configuration is structured to extend beyond a single vertical plane, such as with a protruding nose region and one or more flared regions which extend outwardly, forward or in any of variety of directions. In this regard, it is noted that the precise positioning of the interior securement segments, beyond the preferred orientation to achieve the curved configuration at the goggle region 40, will vary depending upon the particular design requirements of a manufacturer and/or user. As to the specific direction of forces, it is seen that in the preferred embodiments the interior securement segments are positioned such that the forces at the goggle region are generally directed towards the central vertical axis A of the goggle region, thereby tending to generally wrap and/or curve the goggle region 40 over a user's face. Additionally, those forces acting on the perimeter design region 35 are preferably directed generally outwardly from the goggle region 40, thereby providing the enhanced, embellished exterior design to the exterior surface configuration in a manner which protrudes generally from the user's face as well as from the user's head rather than merely wrapping over the user's head like a cap or helmet.

Preferably, the forces directed by the interior securement segments which define the perimeter design region are directed away from the central vertical axis of the goggle region, 40, thereby enabling the perimeter design region 35 to extend in divergent planes relative to a vertical plane of the goggle region 40. Such precise orientation and direction of forces as a result of the inclusion of interior securement segments 52–56 and many interior compartments 25 enables a large variety of three dimensional depictions to ultimately be achieved utilizing the mask assembly 10 of the present invention.

As indicated previously, the interior compartments 25 are preferably disposed in fluid flow communication with one another requiring only a single air inlet port be provided. Moreover, the air inlet port is preferably fitted with a valve assembly 65. While the valve assembly 65 may be a single use, one way valve, it is preferred that it be configured in such a manner as to permit air to be both introduced, either utilizing a user's mouth or through a like assembly, as well as removed from the interior chamber of the mask assembly 10 if storage of the mask assembly 10 is desired for future re-use.

In the preferred embodiment, the decorative mask assembly 10 of the present invention further includes fastening means. Preferably, the fastening means comprise an elastic band 70 having a first end 71 and a second end 72, structured to be coupled with the mask assembly 10. In the preferred embodiment, the elastic band 70 is coupled directly to the first flexible material panel 22 by any conventional fastening means. For example, the elastic band 70 may be heat sealed to the first flexible material panel 22 at an attachment point so long as the heat sealing is such that the first flexible material panel will not be sealed with the second flexible material panel at that same attachment point. In the preferred embodiment, however, the elastic band is coupled to the first flexible material panel 22 utilizing an adhesive material strip 73 or 74. Of course, a glue or like adhesive material, or any other effective means of securing the elastic band 70 thereto such as integral construction may also be utilized. Also, an elastic band 70 need not be utilized as a string or other like fastening means may be incorporated as well as any series of hooks, clips, straps, or other assemblies. Additionally, a rod or other rigid support member could be utilized as fastening means attached to the mask assembly 10, so as to permit a user to more temporarily hold the decorative mask assembly 10 on his or her face.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. To be disposed in confronting relation to a user's face, a decorative mask assembly comprising:
    a first flexible material panel and a second flexible material panel,
    at least one perimeter securement segment defined generally about a perimeter of said first and said second flexible material panels,
    said perimeter securement segment defining an interior chamber between said first and said second flexible material panels, said interior chamber being structured to receive and contain a quantity of a gas therein,
    a plurality of interior securement segments defined between said first and said second flexible material panels, said plurality of interior securement segments at least partially defining a plurality of interior compartments in said interior chamber,
    said plurality of interior securement segments and said plurality of interior compartments defined thereby being structured and disposed relative to one another so as to define predetermined, three-dimensional, ornamental, exterior surface configuration in said second flexible material panel that corresponds to a desired three dimensional depiction, and so as to provide shape defining stiffness to said first and said second flexible material panels upon introduction and containment said gas in said interior compartments of said exterior surface configuration in said second flexible material panel being designed to be visible to others when the mask is worn on a user's face,
    fastening means connected to the mask assembly and structured and disposed to orient and maintain said first flexible material panel in a generally vertical plane, in confronting relation to a user's face, and
    said plurality of interior securement segments being further disposed relative to one another so as to define an interior surface contour of said first flexible material panel which substantially conforms to a curvature of a user's face.

2. A decorative mask assembly as recited in claim 1 wherein said interior securement segments are disposed to define a generally forward, concave, fully reversible configuration.

3. A decorative mask assembly as recited in claim 1 further including a goggle region defined by said plurality of interior securement segments and said plurality of interior compartments defined thereby, said goggle region being structured to be disposed generally over a user's eyes.

4. A decorative mask assembly as recited in claim 3 wherein said goggle region comprises at least one eye region structured to be disposed over a corresponding one of a user's eyes so as to permit viewing therethrough.

5. A decorative mask assembly as recited in claim 3 wherein said goggle region is symmetrical about a central vertical axis so as to substantially conform and maintain said interior surface contour of said first flexible material panel to a curvature of the user's face.

6. A decorative mask assembly as recited in claim 5 wherein said goggle region is dimensionally symmetrical about said central vertical axis as defined by said interior securement segments and said interior compartments defined thereby.

7. A decorative mask assembly as recited in claim 3 wherein said goggle region includes a nose section structured and disposed to substantially confront and correspond to a user's nose.

8. A decorative mask assembly as recited in claim 7 wherein a plurality of interior securement segments define said nose section and are disposed relative to one another so as to tend to maintain said nose section in a generally forward protruding orientation so as to more effectively accommodate a user's nose.

9. A decorative mask assembly as recited in claim 3 wherein at least two of said interior securement segments which define said goggle region converge generally towards a first axis point defined on a central vertical axis of said goggle region so as to effectively define said predetermined, three-dimensional, ornamental, exterior surface configuration in said second flexible material panel that corresponds to said desired three dimensional depiction and so as to define said interior surface contour of said first flexible material panel which conforms to the curvature of a user's face.

10. A decorative mask assembly as recited in claim 9 wherein said at least two of said interior securement segments which define said goggle region and which converge generally towards said first axis point defined on the central vertical axis of said goggle region further define a nose section which tends to be maintained in a generally forward protruding orientation so as to more effectively accommodate a user's nose.

11. A decorative mask assembly as recited in claim 9 wherein said goggle region includes a pair of spaced apart eye regions, said eye regions being symmetrically aligned relative to said central vertical axis of said goggle region.

12. A decorative mask assembly as recited in claim 11 wherein each of said eye regions is defined by an eye perimeter securement segment defined between said first and said second flexible material panels.

13. A decorative mask assembly as recited in claim 12 wherein each of said eye regions is open.

14. A decorative mask assembly as recited in claim 12 wherein said first axis point defined on said central vertical axis is disposed within approximately two inches from said eye perimeter securement segments so as to effectively conform and maintain said interior surface contour of said first flexible material panel to the curvature of a user's face.

15. A decorative mask assembly as recited in claim 11 wherein said first axis point defined on said central vertical axis is further defined generally below a center point of said eye regions.

16. A decorative mask assembly as recited in claim 11 wherein at least two of said interior securement segments which define said goggle region converge generally towards a second axis point defined on said central vertical axis of said goggle region so as to further effectively define said predetermined, three-dimensional, ornamental, exterior surface configuration in said second flexible material panel that corresponds to said desired three dimensional depiction and so as to further define said interior surface contour of said first flexible material panel in conformity with the curvature of a user's face.

17. A decorative mask assembly as recited in claim 16 wherein said second axis point defined on said central vertical axis is defined generally above said center point of said eye regions.

18. A decorative mask assembly as recited in claim 3 further including a perimeter design region disposed radially outward from said goggle region, said perimeter design region structured to provide an embellished, enlarged exterior design to said predetermined, three-dimensional, ornamental, exterior surface configuration which is designed to protrude generally radially from a user's face and head.

19. A decorative mask assembly as recited in claim 18 wherein said perimeter design region is volumetrically symmetric about a central vertical axis thereof.

20. A decorative mask assembly as recited in claim 18 wherein said perimeter design region is dimensionally symmetric about a central vertical axis thereof.

21. A decorative mask assembly as recited in claim 1 wherein said plurality of interior compartments are disposed in fluid flow communication with one another.

22. A decorative mask assembly as recited in claim 21 including at least one exterior inflation port through which the gas is introduced into said interior chamber.

23. A decorative mask assembly as recited in claim 22 wherein said inflation port includes a valve assembly structured to permit inflation and deflation of said interior chamber so as to permit the mask assembly to be re-used.

24. A decorative mask assembly as recited in claim 1 wherein said interior securement segments include a seal defined between said first and said second flexible material panels.

25. A decorative mask assembly as recited in claim 24 wherein said seal is formed directly between said first and said second flexible material panels.

26. A decorative mask assembly as recited in claim 1 wherein said fastening means comprises an elastic band having a first end and a second end coupled to said first flexible material panel, said elastic band being structured to extend about a user's head.

27. A decorative mask assembly as recited in claim 26 wherein each of said first and said second ends of said elastic band are heat sealed directly to said first flexible material panel at separate attachment points without causing said first flexible material panel to be sealed with said second flexible material panel at said attachment points.

28. A decorative mask assembly as recited in claim 27 wherein said first and said second ends of said elastic band are coupled to said first flexible material panel at said attachment points utilizing an adhesive material.

29. A decorative mask assembly as recited in claim 1 wherein said interior securement segments are disposed relative to one another so as to direct forces acting on said first and said second flexible material panels, which result upon inflation of said plurality of interior compartments, in a direction to define said interior surface contour of said first flexible material panel which conforms to the curvature of a user's face and to define said predetermined, three-dimensional, ornamental, exterior surface configuration beyond a single vertical plane.

30. A decorative mask assembly as recited in claim 29 further includes an interior goggle region defined by said plurality of interior securement segments and said plurality of different sized interior compartments defined thereby, said interior goggle region being structured to be disposed generally over a user's eyes.

31. A decorative mask assembly as recited in claim 30 wherein said interior securement segments which define said goggle region are structured and disposed to direct the forces at said goggle region towards a central vertical axis of said goggle region.

32. A decorative mask assembly as recited in claim 31 wherein said interior securement segments which define said goggle region are structured and disposed to direct the forces at said goggle region in a direction that tends to wrap said goggle region around a user's face.

33. A decorative mask assembly as recited in claim 31 including a perimeter design region disposed radially outward from said goggle region, said perimeter design region structured to provide an embellished, enlarged exterior design to said predetermined, three-dimensional, ornamental, exterior surface configuration which is designed to protrude generally radially from a user's face and head.

34. A decorative mask assembly as recited in claim 33 wherein said interior securement segments which define said perimeter design region and which define said goggle region are structured and disposed such that said surface forces at said perimeter design region tend to be directed away from said central vertical axis of said goggle region.

35. A decorative mask assembly as recited in claim 34 wherein said interior securement segments which define said perimeter design region and which define said goggle region are structured and disposed to direct the forces at said perimeter design region in divergent planes relative to a vertical plane of said goggle region so as to enhance said predetermined, three-dimensional, ornamental, exterior surface configuration.

36. To be disposed in confronting relation to a user's face, a decorative mask assembly comprising:
- a first flexible material panel and a second flexible material panel,
- at least one perimeter securement segment defined generally about a perimeter of said first and said second flexible material panels,
- said perimeter securement segment defining an interior chamber between said first and said second flexible material panels, said interior chamber being structured to receive and contain a quantity of a gas therein,
- a plurality of interior securement segments defined between said first and said second flexible material panels, said plurality of interior securement segments at least partially defining a plurality of interior compartments in said interior chamber,
- said plurality of interior securement segments and said plurality of interior compartments defined thereby being structured and disposed relative to one another so as to define a predetermined, three-dimensional, ornamental, exterior surface configuration in said second flexible material panel that corresponds to a desired three dimensional depiction, and so as to provide shape defining stiffness to said first and said second flexible material panels upon introduction and containment of said gas in said interior compartments, said exterior surface configuration in said second flexible material panel being designed to be visible to others when the mask is worn on a user's face
- fastening means connected to the mask assembly and structured and disposed to orient and maintain said first flexible material panel in a generally vertical plane, in confronting relation to a user's face,
- said plurality of interior securement segments being further disposed relative to one another so as to define an interior surface contour of said first flexible material panel which substantially conforms to a curvature of a user's face,
- a goggle region defined by said plurality of interior securement segments and said plurality of interior compartments defined thereby, said goggle region being structured to be disposed generally over a user's eyes,
- a pair of spaced apart eye regions defined in said goggle region, said eye regions being symmetrically aligned relative to a central vertical axis of said goggle region and being structured to be disposed over a user's eyes so as to permit viewing therethrough,
- at least two of said interior securement segments which define said goggle region converging generally towards a first axis point defined on said central vertical axis of said goggle region so as to effectively define said predetermined, three-dimensional, ornamental, exterior surface configuration in said second flexible material panel that corresponds to said desired three dimensional depiction and so as to define said interior surface contour of said first flexible material panel which conforms to the curvature of a user's face, and
- said first axis point being defined generally below a center point of said eye regions.

37. A decorative mask assembly as recited in claim 36 wherein said at least two of said interior securement segments which define said goggle region and which converge generally towards said first axis point defined on the central vertical axis of said goggle region, further define a nose section which tends to be maintained in a generally forward protruding orientation so as to more effectively accommodate a user's nose.

38. A decorative mask assembly as recited in claim 37 wherein each of said eye regions is defined by an eye perimeter securement segment defined between said first and said second flexible material panels.

39. A decorative mask assembly as recited in claim 38 wherein said first axis point is within approximately two inches from said eye perimeter securement segments so as to effectively maintain said interior surface contour of said first flexible material panel which conforms to the curvature of a user's face.

40. To be disposed in confronting relation to a user's face, a decorative mask assembly comprising:
- a first flexible material panel and a second flexible material panel,
- at least one perimeter securement segment defined generally about a perimeter of said first and said second flexible material panels,
- said perimeter securement segment defining an interior chamber between said first and said second flexible material panels, said interior chamber being structured to receive and contain a quantity of a gas therein,
- a plurality of interior securement segments defined between said first and said second flexible material panels, said plurality of interior securement segments at least partially defining a plurality of interior compartments in said interior chamber,
- said plurality of interior securement segments and said plurality of interior compartments defined thereby being structured and disposed relative to one another so as to define a predetermined, three-dimensional, ornamental, exterior surface configuration in said second flexible material panel that corresponds to a desired three dimensional depiction, and so as to provide shape defining stiffness to said first and said second flexible material panels upon introduction and containment of said gas in said interior compartments, said exterior surface configuration in said second flexible material panel being designed to be visible to others when the mask is worn on a user's face fastening means connected to the mask assembly and structured and disposed to orient and maintain said first flexible material panel in a generally vertical plane, in confronting relation to a user's face, said plurality of interior securement segments being further disposed relative to one another so as to define an interior surface contour of said first flexible material panel which substantially conforms to a curvature of a user's face, said interior securement segments being disposed relative to one another so as to direct forces acting on said first and said second flexible material panels, which result upon inflation of said plurality of interior compartments, in a direction to define said interior surface contour of said first flexible material panel which conforms to the curvature of a user's face and to define said predetermined, three-dimensional, ornamental, exterior surface configuration beyond a single vertical plane, an interior goggle region defined by said plurality of interior securement segments and said plurality of interior compartments defined thereby, said interior goggle region being structured to be disposed generally over a user's eyes, said interior securement segments which define said goggle region being structured and disposed to direct the forces at said goggle region towards a central vertical axis of said goggle region so as to tend to wrap said goggle region around a user's face, a perimeter design region disposed radially outward from said goggle region, said perimeter design region structured to provide an embellished, enlarged exterior design to said predetermined, three-dimensional, ornamental, exterior surface configuration which is designed to protrude generally radially from a user's face and head, and said interior securement segments which define said perimeter design region and which define said goggle region being structured and disposed such that said surface forces at said perimeter design region tend to be directed away from said central vertical axis of said goggle region.

41. A decorative mask assembly as recited in claim 40 wherein said interior securement segments which define said perimeter design region and which define said goggle region are structured and disposed to direct the forces at said perimeter design region in divergent planes relative to a vertical plane of said goggle region so as to enhance said predetermined, three-dimensional, ornamental, exterior surface configuration.

42. A decorative mask assembly as recited in claim 40 wherein at least one of said interior securement segments is structured to generally isolate said goggle region from said perimeter design region and thereby generally isolate said surface forces at said goggle region from said surface forces at said perimeter design region.

* * * * *

UNITED STATES PATENT AND TRADEMARK OFFICE
CERTIFICATE OF CORRECTION

PATENT NO.   : 5,787,508
DATED        : August 4, 1998
INVENTOR(S)  : Ruben D. Gattamorta It is certified that error appears in the above-indentified patent and that said Letters Patent is hereby corrected as shown below:

On the title page: Item [63] Related U.S. Application Continuation-in-part of Ser. No. 467,104, June 6, 1995.--

Column 1, Line 4, insert --The present application is a continuation-in-part of co-pending U.S. Patent Application Serial No. 08/467,104 filed June 6, 1995.--

Signed and Sealed this

Second Day of February, 1999

Attest:

Attesting Officer

*Acting Commissioner of Patents and Trademarks*